(12) United States Patent
Collins

(10) Patent No.: US 11,110,258 B1
(45) Date of Patent: Sep. 7, 2021

(54) LIQUID ANTIMICROBIAL DELIVERY SYSTEM (L.A.D.S.) TO HELP IMPROVE AUTOIMMUNE REGULATION

(71) Applicant: Virgil Collins, Richmond Heights, OH (US)

(72) Inventor: Virgil Collins, Richmond Heights, OH (US)

( * ) Notice: Subject to any disclaimer, the term of this patent is extended or adjusted under 35 U.S.C. 154(b) by 0 days.

(21) Appl. No.: 17/239,808

(22) Filed: Apr. 26, 2021

(51) Int. Cl.
| | |
|---|---|
| *A61M 35/00* | (2006.01) |
| *A61Q 17/00* | (2006.01) |
| *A61K 8/34* | (2006.01) |
| *A61K 8/97* | (2017.01) |
| *A61M 21/02* | (2006.01) |
| *A41D 19/00* | (2006.01) |
| *A61K 8/22* | (2006.01) |
| *A61M 21/00* | (2006.01) |

(52) U.S. Cl.
CPC ........... *A61M 35/10* (2019.05); *A41D 19/002* (2013.01); *A61K 8/22* (2013.01); *A61K 8/34* (2013.01); *A61K 8/97* (2013.01); *A61M 21/02* (2013.01); *A61Q 17/005* (2013.01); *A61K 2800/87* (2013.01); *A61M 2021/0016* (2013.01)

(58) Field of Classification Search
CPC ................................ A41D 13/11; A41D 19/00
USPC ............................. 222/92; 2/159, 161.7, 173
See application file for complete search history.

(56) References Cited

U.S. PATENT DOCUMENTS

| 4,586,635 A | * | 5/1986 | Collins, Jr. | ............ B65D 35/28 222/105 |
|---|---|---|---|---|
| 5,181,539 A | * | 1/1993 | Yokoyama | ................ F16K 5/06 137/625.32 |
| 6,626,202 B1 | * | 9/2003 | Harvey | ..................... E03B 7/12 137/62 |

* cited by examiner

*Primary Examiner* — Walter E Webb
(74) *Attorney, Agent, or Firm* — Daniel M. Cohn; Howard M. Cohn

(57) ABSTRACT

A Liquid Antimicrobial Delivery System includes a measured amount of anti-microbial fluids, and an anti-bacteria glove having one or more liquid storage patches to store the anti-microbial fluids. A collapsible tube container utilizing a ball and stem applicator delivers a predetermined amount of the anti-microbial fluid. The collapsible tube has a conical dome opening with first and second shut-off valves. Finally, a face mask includes a liquid storage patch to store the anti-microbial fluids.

15 Claims, 8 Drawing Sheets

LIQUID ANTIMICROBIAL DELIVERY SYSTEM (L.A.D.S.) TO HELP IMPROVE AUTOIMMUNE REGULATION

FIELD OF INVENTION

The present invention relates generally to a liquid antimicrobial delivery system, and, more specifically, the present invention relates to a device that delivers a measured amount of anti-microbial fluids for the purpose of building the immune system.

BACKGROUND OF INVENTION

Immunologists and scientists have established two theories as to why people living in high income countries are so susceptible to diseases, and have shown an increase in: (1) allergies, (2) inflammatory bowel diseases, and (3) autoimmunity diseases (e.g. type 1 diabetes and multiple sclerosis).

In 1989 Professor David Strachan came up with a theory that he named "the Hygiene Hypothesis" where he claimed that the reason for the increase in infections in society was that we are "too clean" and not being exposed early in childhood to infectious agents, symbiotic microorganisms (such as the gut flora or probiotics), and parasites. This lack of exposure was believed to lead to defects in establishing the proper immune tolerance in our system.

In 2003 Professor Graham Rook established a new theory known as the "Old Friends Mechanism" hypothesis that provided an alternative to the "Hygiene Hypothesis. His theory is that our immune system depends on certain microbes that evolved together with the human organism which are now not readily available in our modern society. He described the missing microbes as "Old Friends" of our immune system, and this absence causes abnormal functionality of our immune system.

There is now evidence that the simultaneous increase in diseases is at least partly attributable to malfunction of regulatory T Cells which make up our immune system. Both theories suggest that because modern society is not being exposed to a diversity of certain sorts of microbiotas and bacteria it causes the autoimmune system to turn to fighting allergens in the body because it lacks the external microbes it needs.

Several studies have been conducted that show that people who live on farms are exposed to more microbes and as a result the immune system adds more "T Cells" (lymphocytes) to fight those microbes, and the autoimmune system of the body doesn't have to fight allergens.

SUMMARY OF THE INVENTION

According to an embodiment of the present invention, there is disclosed a Liquid Antimicrobial Delivery System designed to provide protection to a user exposed to bacteria. The Liquid Antimicrobial Delivery System includes a measured amount of anti-microbial fluids, and an anti-bacteria glove having one or more liquid storage patches to store the anti-microbial fluids. A collapsible tube container utilizing a ball and stem applicator delivers a predetermined amount of the anti-microbial fluid. The collapsible tube has a conical dome opening with first and second shut-off valves. Finally, a face mask includes a liquid storage patch to store the anti-microbial fluids.

According to a further embodiment of the present invention, there is disclosed an anti-bacteria glove designed to store a measured amount of anti-microbial fluids to protect a user from contamination from bacterial diseases. The anti-bacteria glove includes a fingerless glove body including a palm portion, and a top portion. One or more liquid storage patches are included to absorb the anti-microbial fluids. A band is disposed about a first opening of the glove body, and a band disposed about a second opening of the glove body, each to prevent microbes from entering the glove to reach the user. Finally, a band is disposed about a thumb opening to prevent microbes from entering the glove to reach the user.

According to a further embodiment of the present invention, there is disclosed a collapsible tube container designed to store and dispense anti-microbial fluids to protect a user from contamination from bacterial diseases. The collapsible tube container includes a tubular body portion, having a hollow opening to contain the anti-microbial fluid therein, and a conical dome opening. A ball and stem applicator delivers a predetermined amount of anti-microbial fluid to a user. The collapsible tube has a conical dome opening with first and second shut-off valves. Finally, a conical dome cap temporarily seals the anti-microbial fluid within the tubular body portion.

BRIEF DESCRIPTION OF THE DRAWINGS

The structure, operation, and advantages of the present invention will become further apparent upon consideration of the following description taken in conjunction with the accompanying figures (Figures). The figures are intended to be illustrative, not limiting. Certain elements in some of the figures may be omitted, or illustrated not-to-scale, for illustrative clarity. The cross-sectional views may be in the form of slices, or near-sighted cross-sectional views, omitting certain background lines which would otherwise be visible in a true cross-sectional view, for illustrative clarity.

Often, similar elements may be referred to by similar numbers in various figures (Figures) of the drawing, in which case typically the last two significant digits may be the same, the most significant digit being the number of the drawing figure (Figure).

DETAILED DESCRIPTION OF THE PREFERRED EMBODIMENT

Figure 1:
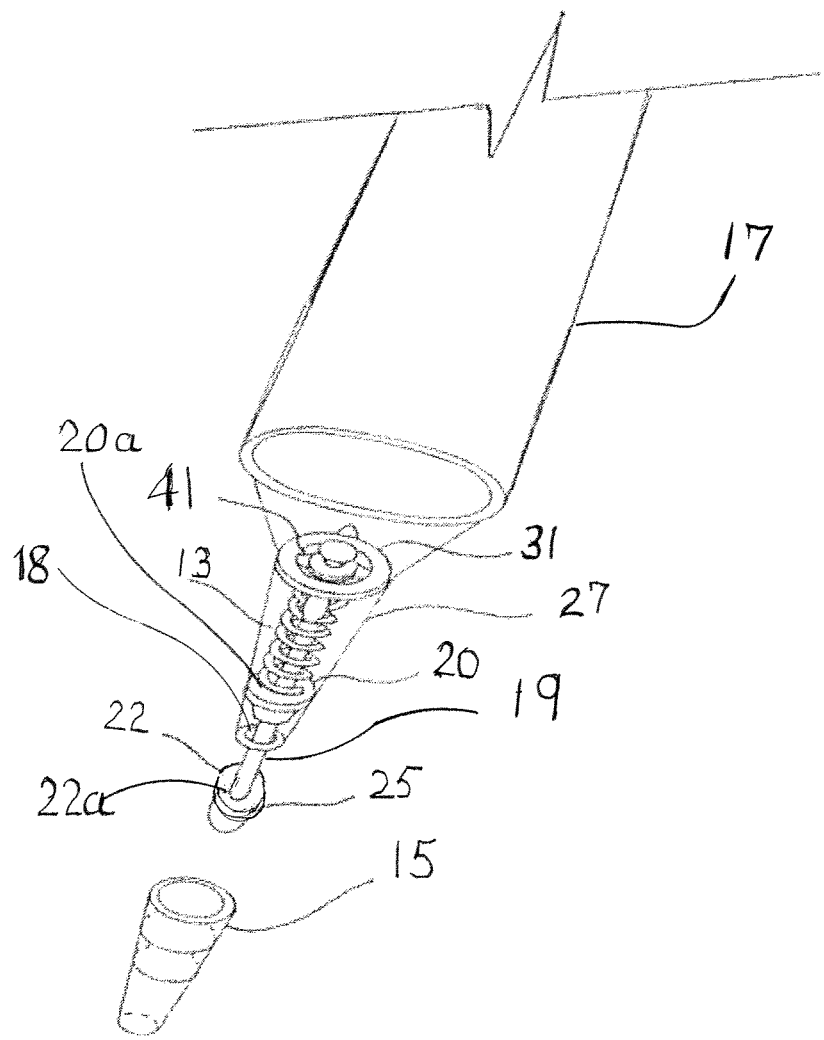
FIG. 1 is a cross sectional cut way view of the conical dome of the collapsible tube container with the double shut-off ball and stem dispensing mechanism as used in the Liquid Antimicrobial Delivery System (L.A.D.S.), according to the present invention.

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

Gloves serve a variety of purposes, for example protecting individual's hands from becoming dirty and from contacting germs. Protective gloves are commonly used by medical personnel (such as doctors, nurses, dentists and emergency workers), food service personnel, sanitation personnel, maintenance personnel and many others, in order to protect themselves and others from contaminants and diseases. Such gloves are expected to provide a barrier between the wearer and the environment with which the glove comes in contact.

The Liquid Antimicrobial Delivery System (L.A.D.S.) utilizes anti-bacteria gloves 10 and a collapsible tube container 17 in a novel and unique manner, allowing users such as nurses, medical personnel, and anyone else who is constantly exposed to bacteria to have protection against harmful diseases. Bacterial diseases include any type of illness caused by bacteria. Bacteria are a type of microorganism, which are tiny forms of life that can only be seen with a microscope. Other types of microorganisms include viruses, some fungi, and some parasites. Harmful bacteria that cause bacterial infections and disease are called pathogenic bacteria. Bacterial diseases occur when pathogenic bacteria get into the body and begin to reproduce and crowd out healthy bacteria, or to grow in tissues that are normally sterile. Harmful bacteria may also emit toxins that damage the body.

In general terms, the L.A.D.S. is devised to deliver a measured amount of anti-microbial fluids to a user, for the purpose of building the immune system by protecting the hands, ears, and nose from microbial invasion. The anti-microbial fluids may be any appropriate liquid. Preferably, the liquid is a phytoncide, isopropyl alcohol, hydrogen peroxide, or any other liquids for protection against virus and diseases.

The L.A.D.S. consists of a collapsible tube container 17, having a conical dome opening 18 with first and second shut-off valves 20 and 22 for controlling the amount of liquid dispensed with each jab of the ball & stem applicator. The collapsible tube container 17 is designed to deliver a predetermined amount of the liquid directly to the skin of the user, and to an anti-bacterial glove 10, as described hereinafter.

Figure 4:
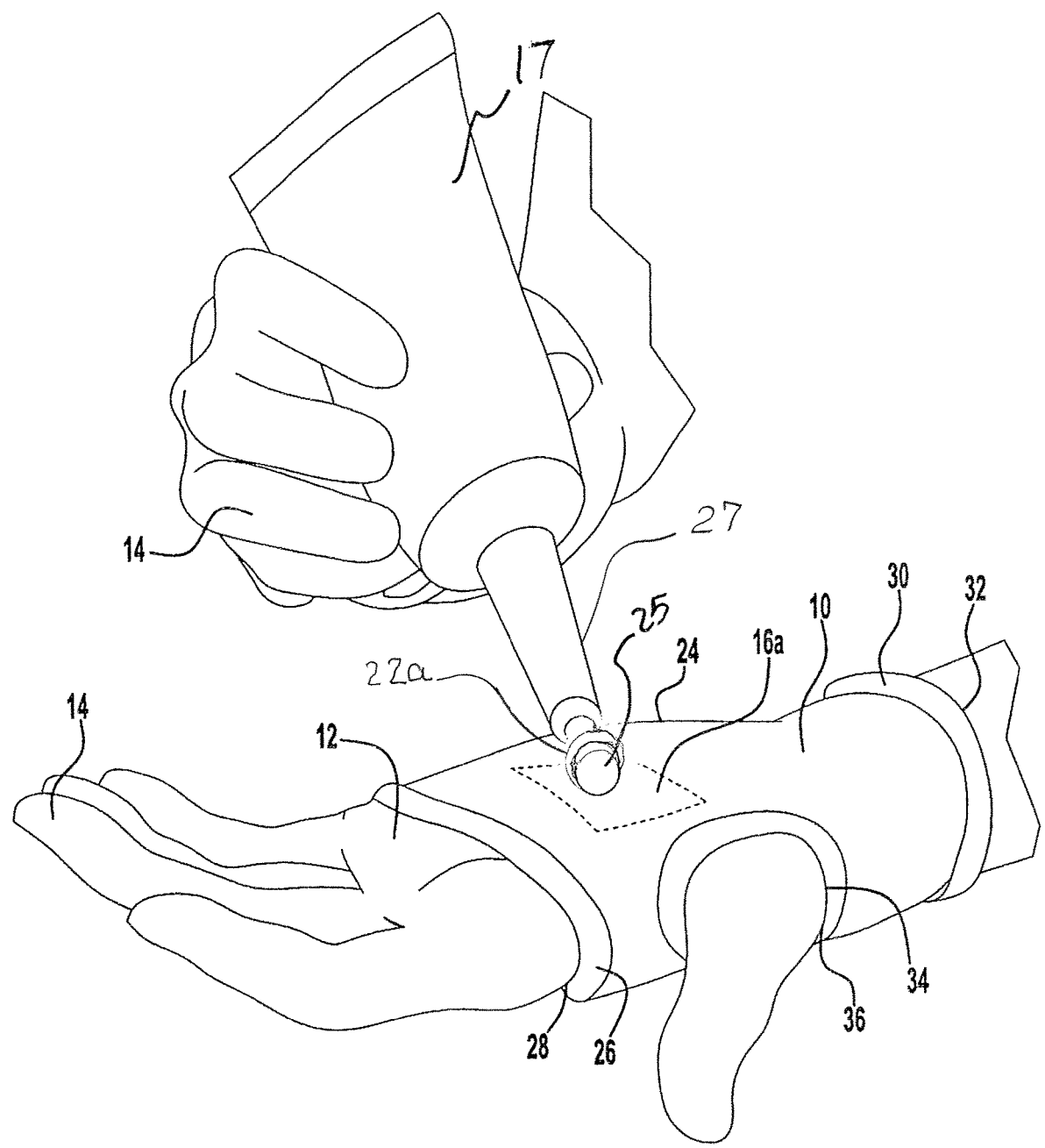
FIG. 4 is a front, three-dimensional view of the anti-bacteria glove used as an element of the L.A.D.S. in use, according to the present invention.

FIG. 4 illustrates a top view of the fingerless, anti-bacterial glove 10. In general terms, the anti-bacterial glove 10 is designed to protect the user's hands 12 and fingers 14 from contamination from bacterial diseases. These may include colds, the flu, and viruses. This is accomplished by providing one or more liquid storage patches 16a and 16b. As described hereinafter, liquid storage patches 16a is located on the palm portion 23 of the glove 10, and liquid storage patches 16b is located on the top portion 21 of the glove. Liquid is dispensed in a predetermined amount from the collapsible tube container 17 onto the liquid storage patches 16a and 16b, where it is stored. Where the basic hand sanitizer may provide protection for only 20 seconds, the L.A.D.S. antibacterial gloves can provide protection for up 10 minutes with the stored sanitizer.

Figure 2:
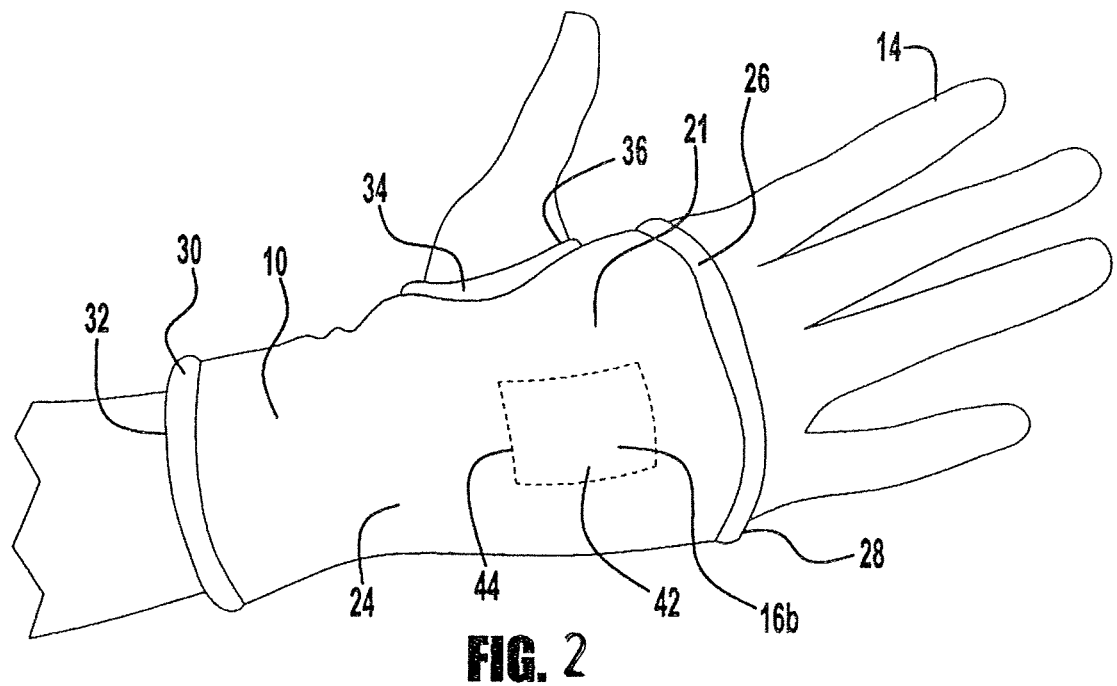
FIG. 2 is a top view of the anti-bacteria glove used as an element of the L.A.D.S., according to the present invention.
Figure 3:
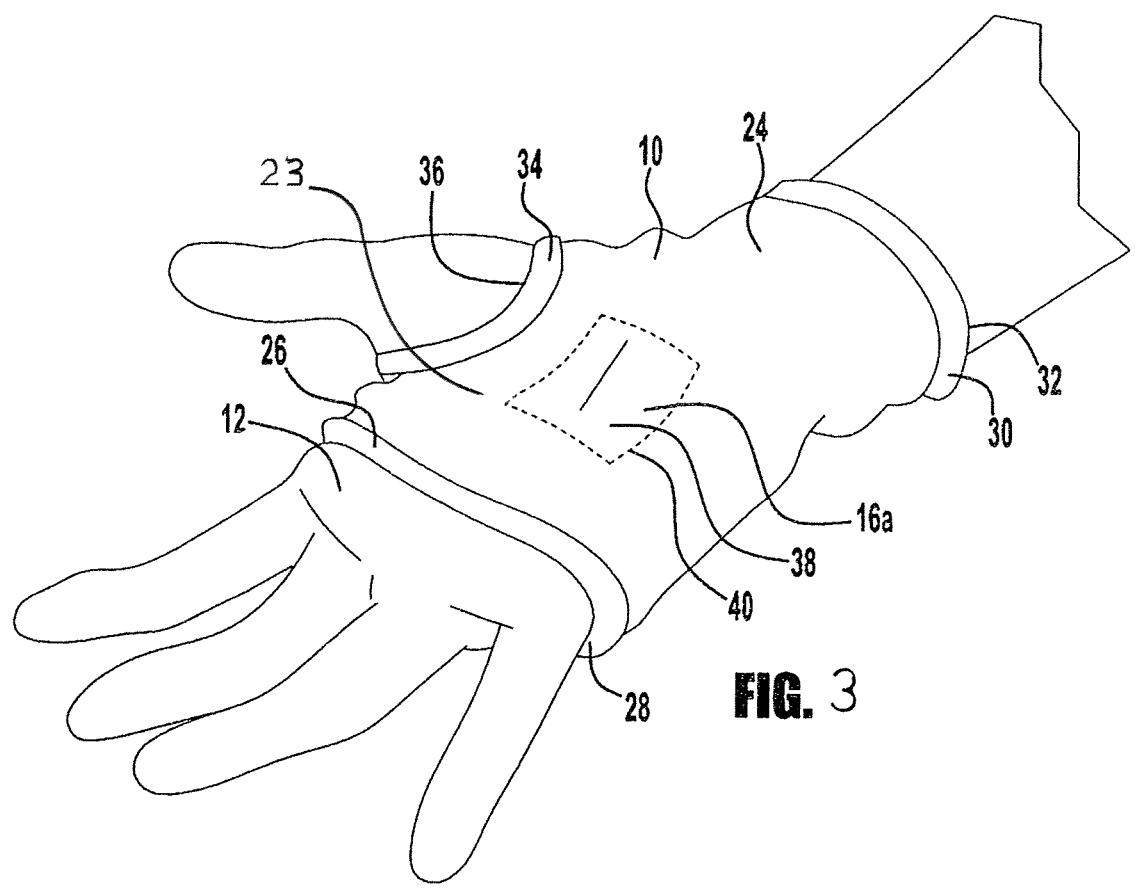
FIG. 3 is a bottom view of the anti-bacterial glove used as an element of the L.A.D.S., according to the present invention.

As seen in FIGS. 2 and 3, the anti-bacterial glove 10 comprises a fingerless glove body 24. The glove body 24 includes the palm portion 23, whereupon the liquid storage patch 16a is disposed, and a top portion 21 where storage patch 16b is disposed. Typically, the glove body 24 does not contain finger covering portions. However, it is within the terms of the embodiment that there be finger covering portions, although not illustrated in the Figure.

There is a band 26 disposed about the first opening 28 of the glove 10, and a band 30 disposed about the second opening 32 of the glove. The bands 26 and 30 may be elasticized to tightly enclose the user's hand 12 so as to prevent microbes from entering the glove 10. Further, there may be a band 34 around the thumb opening 36 to further prevent microbes from entering the glove 10 to reach the hand 12 of the user.

The glove body 24 is preferably sized to fit tightly over a wearer's hand. It must be noted that the anti-bacterial glove 10 may come in a variety of different sizes to accommodate the hands 12 of a variety of users. Alternatively, the anti-bacterial glove 10 may be constructed of a stretch material to accommodate a plurality of hand 12 sizes.

The anti-bacterial glove 10 should have a wall thickness sufficient to guard against rips and tears, but should also be sufficiently thin to retain dexterity and feel. For example, the anti-bacterial glove 10 may have a wall thickness between about 0.0625 inches and 0.25 inches.

The anti-bacterial glove 10 may be constructed of any desired material, such as stretchable neoprene. It is within the terms of the embodiment, that the material forming the anti-bacterial glove 10 be sterilize able so that the glove may be sterilized and reused. Alternatively, the anti-bacterial glove 10 may be constructed of a thinner material, such as latex, and the anti-bacterial glove 10 may be considered disposable.

The liquid storage patches 16a and 16b located on the palm portion 23 and top portion 21 of the anti-bacterial glove 10, respectively, designed to store liquid therein, such as isopropyl alcohol. The liquid storage patches 16a and 16b are constructed of a material which will absorb a dose or charge of liquid from the tube container 17. The liquid storage patches 16a and 16b are typically square or rectangular in shape, although any appropriate shape may be utilized, and may be of any desired dimensions. For example, the liquid storage patch 16a and 16b may have a length with a range between 1.75 inches and 2.0 inches, and a width with a range between 1.50 inches and 1.75 inches.

The liquid storage patch 16a has an exterior side 38, and an interior side 40. Similarly, the liquid storage patch 16b has an exterior side 42, and an interior side 44. The interior sides 40 and 44 of the patches 16a and 16b, respectively, are each adjacent to the palm and top of the user's hand, respectively. The exterior sides 38 and 42 of the patches 16a and 16b, respectively, are each designed to be of an absorbent material, to accept a dose of the liquid from the tube container 17. By contrast, the interior sides 40 and 44 of the patches 16a and 16b, respectively, are sealed to prevent the liquid from coming in contact with the user's hand. An exemplary material for the interior sides 40 and 44 is Velcro.

Figure 10:
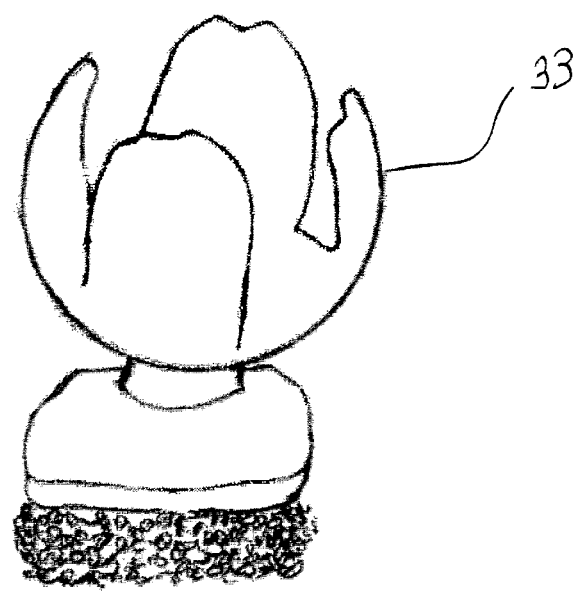
FIG. 10 is a perspective view of a Snap-On Sponge attachment used as an element of the L.A.D.S., according to the present invention.
Figure 11:
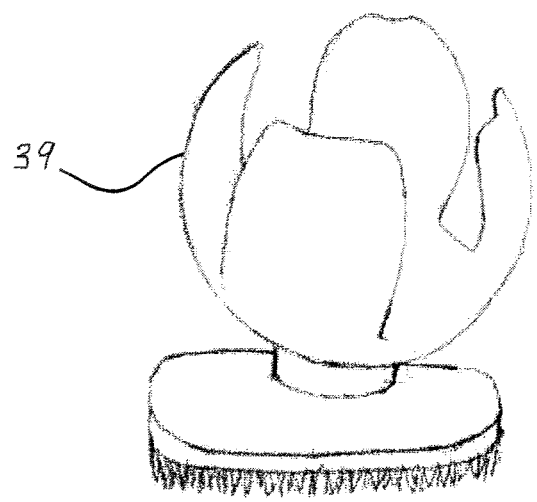
FIG. 11 is a perspective view of a Snap-On Brush attachment used as an element of the L.A.D.S., according to the present invention.
Figure 12:
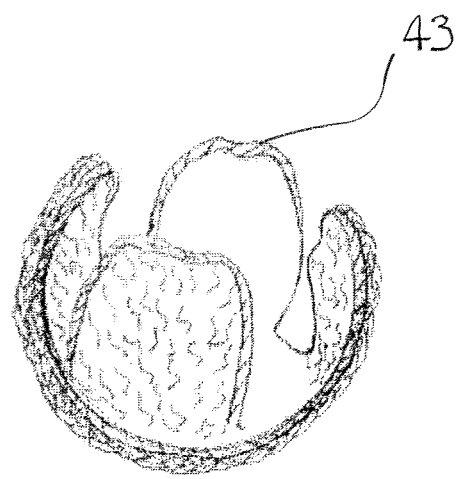
FIG. 12 is a perspective view of a Snap-On Cotton Ball attachment used as an element of the L.A.D.S., according to the present invention.

The liquid storage patches 16a and 16b may receive the liquid from any desired source. In the preferred embodiment, as illustrated in FIG. 4, the liquid storage patches 16a and 16b receive the liquid from the ball and stem applicator 25a of the collapsible tube container 17. The ball 25 of the Ball and Stem applicator 25a is constructed of a hard acrylic material to accommodate Snap-On attachments such as the sponge 33 attachment shown in FIG. 10, the Snap-on brush 39 attachment shown in FIG. 11, or the Snap-on cotton ball 43 attachment shown in FIG. 12. These attachments can be used to sanitize medical apparatus such as catheters and dialysis equipment or other medical needs. These Snap-on attachments are also useful for protecting pets and animals from infections.

Figure 8:
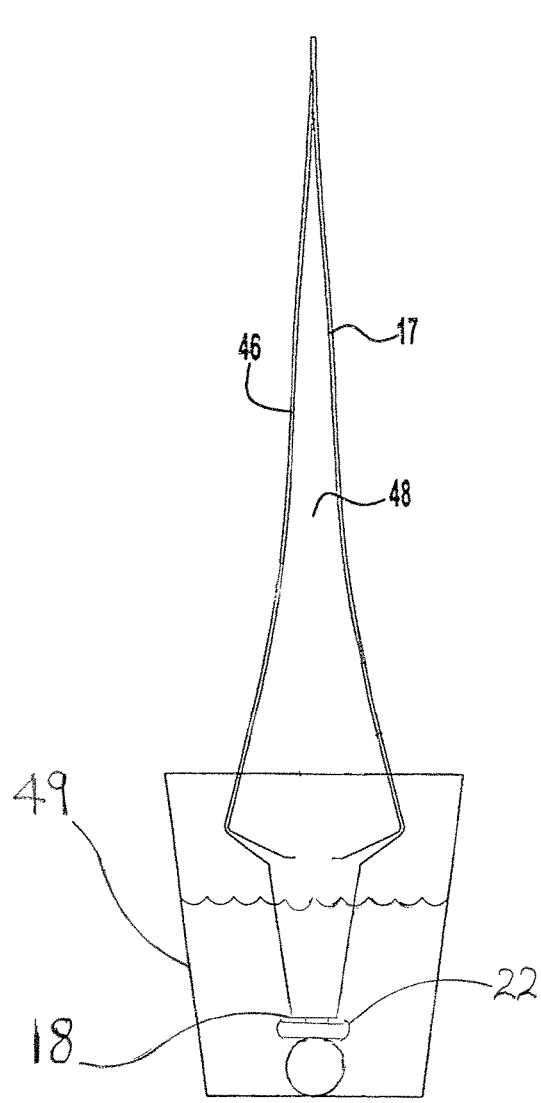
FIG. 8 is a front view of the L.A.D.S. delivery device in an empty state, according to the present invention.
Figure 9:
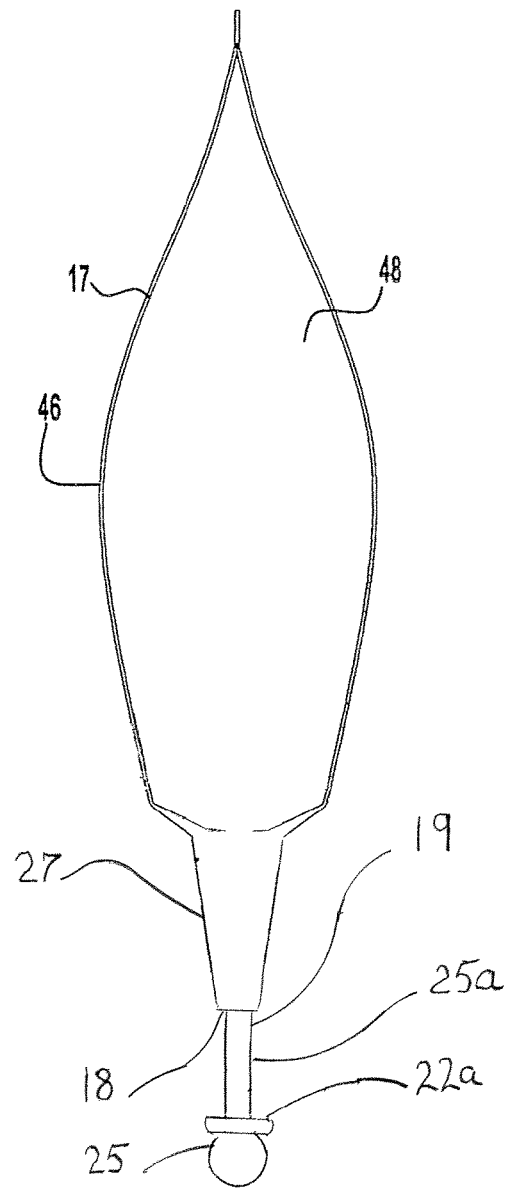
FIG. 9 is a front view of the L.A.D.S. delivery device in a full state, according to the present invention.

As illustrated in FIGS. 8 and 9, the collapsible tube container 17 of the Liquid Antimicrobial Delivery System (L.A.D.S.) uses a ball and stem applicator 25a to dispense the liquid therein. The tube container consists of a tubular body portion 46, having a hollow opening 48 to contain the liquid therein, and a conical dome opening 18. The tubular body portion 46 may hold any desired amount of liquid, preferably approximately 3 ounces.

The ball and stem applicator 25a of the container 17 includes first and second shut-off valves 20 and 22 and a stem 19 connecting these two valves. The first shut-off valve 20 is shaped as a plunger and is attached to O-ring 20a, and the second shut-off valve 22 is attached to the acrylic ball 25 and O-ring 22a. The ball and stem applicator 25a is designed to control the amount of liquid dispensed with each jab of the ball & stem applicator 25a. Although not shown, the collapsible tube container 17 may contain attachments to allow the user to carry the tube around the neck, or be attached to a belt clip.

When the ball 25 is jabbed against the skin or a surface, such as one of the liquid patches 16a and 16b, a shot of liquid is released from the body portion 46 of the tube container 17. The collapsible tube container 17 is designed to deliver a predetermined amount of the antimicrobial liquid directly to the skin of the user, or to the antibacterial glove 10, or to a medical device, with every jab of the Ball and Stem Applicator 25a.

As noted, the ball and stem applicator 25a of the collapsible tube container 17 is designed to dispense a predetermined amount of liquid. For example, a preferential amount of liquid to be dispensed may be 1.25 milliliters of liquid with each jab of the ball & stem applicator 25a with a "full" jab. Further, approximately 4.5 milliliters may be dispensed with a "half" jab while simultaneously squeezing the collapsible tube container 17. The length of the stem 19 determines the amount of liquid to be displaced from the collapsible tube container 17.

FIG. 8 illustrates the refilling features of the present invention. FIG. 8 shows a first condition of the collapsible tube container 17, where there is no liquid contained within the tubular body portion 46. To fill the body portion 46 with liquid, the second shut-off valve 22 is submerged within a container 49 containing the liquid. While simultaneously pressing down on the Ball 25 to open valve 20a, the user squeezes the thin sides of body portion 46, thereby creating a vacuum effect. By partially opening the first shut-off valve 20, the O-ring 20a is opened allowing the fluid to be drawn up into the tube through the conical dome opening 18. Then, the liquid enters into the body portion 46 because the first shut-off valve 20 and O-ring 20a has been opening of Ball and Stem Applicator 25a to the half-way point.

FIG. 9 illustrates a second condition of the collapsible tube container 17, where there is liquid contained within the tubular body portion 46. Further, the first shutoff valve 20 is seated within the conical dome with O-ring 20a. Thus, the liquid within the collapsible tube container 17 remains therein.

The ball and stem applicator 25a operates such that a shot of liquid is dispensed with every "jab" of the applicator 25a that opens the first shut-off valve 20a at the beginning of the "jab, and closes the second shut-off valve 22a at the end of the "jab". The Ball and Stem Applicator 25a is retained in the conical dome 27 of the tube by retainer 31 and guide 41. The time between the open of valve 20a to the closing of vale 22a and the length of valve Stem 19, determines the amount of liquid dispensed at every "jab". A jab is the motion made similar to jabs made with a syringe when injecting a vaccine into an arm.

In use, the ball and stem applicator 25a is used to dispense liquid from within the collapsible tube container 17, in the method discussed hereinabove. The applicator 25a dispenses the liquid to the liquid storage patches 16a and 16b. The storage patch 16a serves to kill bacteria of items that the user touches. Also, as previously noted, the ball and stem applicator 25a can dispense liquid directly to the use's body.

In Japan there is a popular location where people from all over the world go to improve the health of their immune system. The practice is called 'Forest Bathing" where they go to a forest with many ancient trees that give off a fragrance called phytoncide that has been scientifically proven to improve your immune system. The storage patch 16b of L.A.D.S. serves to allow the user to inject liquid phytoncide to inhale for the aromatherapy effect of "Forest Bathing. The storage patch 16b helps the user to build their autoimmune system through the day while attending to basic activities.

Figure 13:
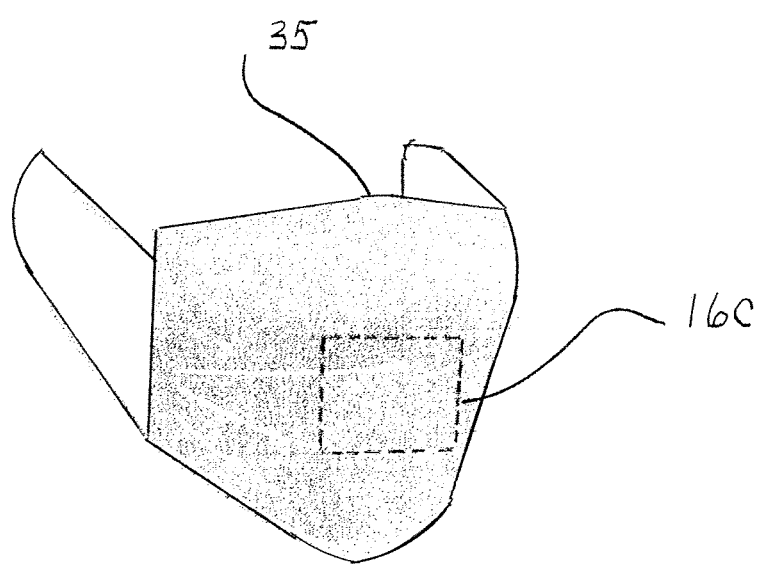
FIG. 13 is a perspective view of an Aromatherapy Face Mask used as an element of the L.A.D.S., according to the present invention.

FIG. 13 is an illustrative view of the aromatherapy face mask 35, as an element of the present invention. This face mask 35 includes a liquid storage patch 16c that stores liquids and oils such as phytoncide to provide aromatherapy for building the immune system and better autoimmune regulation.

Figure 7:
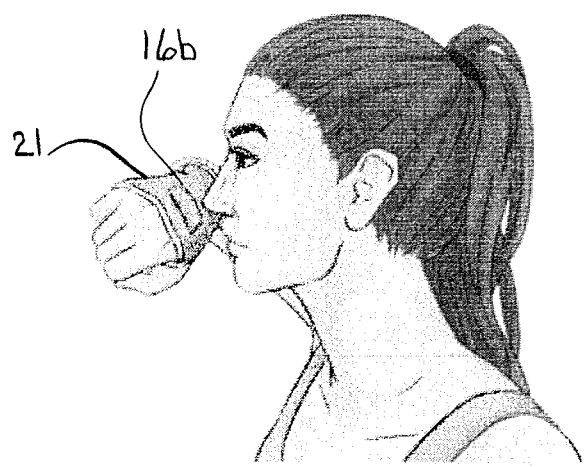
FIG. 7 is an illustrative view of the L.A.D.S. being applied for personal protection, according to present invention.
Figure 6:
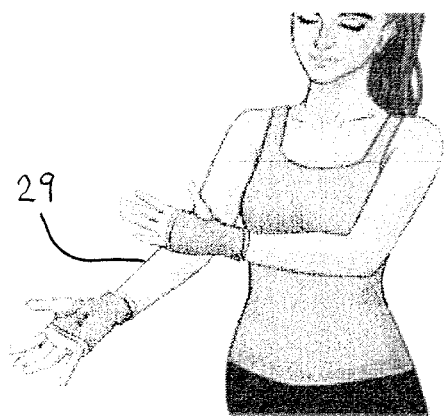
FIG. 6 is an illustrative view of the L.A.D.S. being applied for personal protection, according to the present invention.
Figure 5:
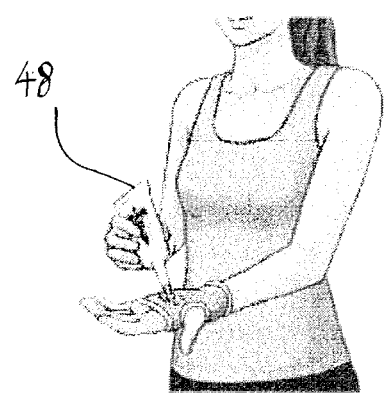
FIG. 5 is an illustrative view of the L.A.D.S. being applied to anti-bacteria glove used as an element of the L.A.D.S., according to the present invention.

FIGS. 5, 6, and 7, are illustrations of the use of L.A.D.S. for personal protection to arms 29 and hands, as an element of the present invention.

When not in use, a conical dome cap 15 pushes against the spring 13 loaded Ball and Stem Applicator up into the tube closing the second shut-off valve 22a sealing the tube shut and leak proof with the double closure of valve 22a and the conical dome cap allowing the tube to be safely carried without leaks.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above-described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A Liquid Antimicrobial Delivery System designed to provide protection to a user exposed to bacteria, comprising;
   a measured amount of anti-microbial fluids;
   an anti-bacteria glove having one or more liquid storage patches to store the anti-microbial fluids;
   a collapsible tube container utilizing a ball and stem applicator to deliver a predetermined amount of the anti-microbial fluid;
   the collapsible tube having a conical dome opening with first and second shut-off valves;
   and
   a face mask includes a liquid storage patch to store the anti-microbial fluids.

2. The Liquid Antimicrobial Delivery System of claim 1, wherein the anti-microbial fluids is chosen from a group consisting of phytoncide, isopropyl alcohol, and hydrogen peroxide.

3. The Liquid Antimicrobial Delivery System of claim 1, wherein the one or more liquid storage patches are disposed on a palm portion and a top portion of the anti-bacteria glove.

4. The Liquid Antimicrobial Delivery System of claim 3, wherein there is a band disposed about a first opening of the anti-bacteria glove 10, and a band disposed about a second opening of the anti-bacteria glove to prevent microbes from entering the glove.

5. The Liquid Antimicrobial Delivery System of claim 4, wherein the one or more liquid storage patches has an exterior side, and an interior side.

6. The Liquid Antimicrobial Delivery System of claim 5, wherein the exterior side is formed of an absorbent material to accept the anti-microbial fluids, and the interior side is sealed to prevent leakage of the anti-microbial fluids.

7. The Liquid Antimicrobial Delivery System of claim 1, wherein the ball and stem applicator of the container includes first and second shut-off valves and a stem connecting the two valves.

8. The Liquid Antimicrobial Delivery System of claim 7, wherein the first shut-off valve is shaped as a plunger and is attached to an O-ring, and the second shut-off valve is attached to an acrylic ball and an O-ring.

9. The Liquid Antimicrobial Delivery System of claim 8, wherein the ball of the Ball and Stem applicator is constructed of a hard acrylic material to accommodate attachments from a group consisting of a sponge attachment, a brush attachment, and a cotton ball attachment.

10. The Liquid Antimicrobial Delivery System of claim 9, wherein the tube container consists of a tubular body portion, having a hollow opening to contain the anti-microbial fluid therein, and a conical dome opening.

11. The Liquid Antimicrobial Delivery System of claim 10, wherein the predetermined amount of the anti-microbial fluid to be delivered from the tube container is 1.25 milliliters of the anti-microbial fluid.

12. An anti-bacteria glove designed to store a measured amount of anti-microbial fluids to protect a user from contamination from bacterial diseases, comprising;
   a fingerless glove body;
   the glove body including a palm portion, and a top portion;
   one or more liquid storage patches to absorb the anti-microbial fluids;
   a band disposed about a first opening of the glove body, and a band disposed about a second opening of the glove body, each to prevent microbes from entering the glove to reach the user; and
   a band disposed about a thumb opening to prevent microbes from entering the glove to reach the user.

13. The Liquid Antimicrobial Delivery System of claim 12, wherein the one or more liquid storage patches are disposed on a palm portion and a top portion of the anti-bacteria glove.

14. The Liquid Antimicrobial Delivery System of claim 13, wherein the one or more liquid storage patches has an exterior side, and an interior side.

15. The Liquid Antimicrobial Delivery System of claim 14, wherein the exterior side is formed of an absorbent material to accept the anti-microbial fluids, and the interior side is sealed to prevent leakage of the anti-microbial fluids.

* * * * *